United States Patent [19]

Lin et al.

[11] 4,374,285

[45] Feb. 15, 1983

[54] SYNTHESIS OF ETHANOL BY HOMOLOGATION OF METHANOL

[75] Inventors: Jiang-Jen Lin; John F. Knifton, both of Austin, Tex.

[73] Assignee: Texaco Inc., White Plains, N.Y.

[21] Appl. No.: 223,514

[22] Filed: Jan. 8, 1981

[51] Int. Cl.$^3$ ............................................. C07C 27/00
[52] U.S. Cl. .................................................. 568/902
[58] Field of Search ......................................... 568/902

[56] References Cited

U.S. PATENT DOCUMENTS 3,285,948  11/1966  Butter .................................. 568/902
4,239,924  12/1980  Pretzer et al. ...................... 568/902
4,277,634   7/1981  Walker ................................ 568/902

*Primary Examiner*—Alan Siegel
*Attorney, Agent, or Firm*—Jack H. Park; Walter D. Hunter

[57] ABSTRACT

Ethanol is prepared by contacting methanol, hydrogen and carbon monoxide with a catalyst system comprising a ruthenium compound, a quaternary phosphonium or ammonium base or salt and a cobalt compound such as cobalt iodide.

22 Claims, No Drawings

SYNTHESIS OF ETHANOL BY HOMOLOGATION OF METHANOL

BACKGROUND OF THE INVENTION

1. FIELD OF THE INVENTION

This invention relates to an improved process for preparing ethanol from methanol by reaction with hydrogen and carbon monoxide.

2. PRIOR ART

A great number of processes have been described in the art for reacting methanol with carbon monoxide and hydrogen in the presence of catalyst systems to produce ethanol. A general disadvantage of the art described processes is that they all produce a wide variety of other related products such as higher molecular weight alcohols, aldehydes, ketones, carboxylic acids, esters, etc. in addition to the desired ethanol.

In U.S. Pat. No. 3,285,948, for example, a method of forming alcohols is set out in which a cobalt catalyst system comprising cobalt carbonyl, an iodine promoter and a ruthenium halide is described. Cawse discloses in U.S. Pat. No. 4,013,700 a process for preparing polyhydric alcohols, etc. by reacting hydrogen and carbon monoxide in the presence of a quaternary phosphonium salt and a rhodium carbonyl at elevated temperature and pressure. Riley et al teach in U.S. Pat. No. 3,248,432 the preparation of ethanol by the reaction of methanol, carbon monoxide, and hydrogen in the presence of a cobalt compound and an iodine promoter. Likewise in British Pat. No. 1,546,428 the preparation of ethanol by reacting methanol with carbon monoxide and hydrogen in the presence of a solvent such as hydrocarbon solvent, a cobalt-containing catalyst such as cobalt iodide or bromide and a tertiary phosphine. Slinkard in U.S. Pat. No. 4,168,391 teaches a process for preparing ethanol by reaction of carbon monoxide, hydrogen and methanol in the presence of cobalt carbonyl and an oxygenated solvent such as dioxane.

All of the processes described above suffer from one or more disadvantages. In most cases the conversion of methanol is low and a wide variety of products in addition to the desired ethanol are formed with consequent separation and disposal problems.

SUMMARY OF THE INVENTION

In the process of this invention ethanol is prepared in high yield by reacting methanol with a mixture of hydrogen and carbon monoxide. More particularly, this invention relates to a process for preparing ethanol by contacting methanol, hydrogen and carbon monoxide with a catalyst system comprising a ruthenium compound, a quaternary phosphonium or ammonium base or salt and a cobalt compound such as cobalt iodide at an elevated temperature and pressure.

Recovery of ethanol from the reaction product can be carried out in any conventional or convenient manner such as by distillation, extraction, etc.

DETAILED DESCRIPTION OF THE INVENTION

The catalyst systems suitable for the practice of this invention comprises a ruthenium compound, a quaternary phosphonium base or salt and a cobalt compound as exemplified by cobalt iodide. These catalyst systems give substantially higher yields of ethanol than can be obtained when the catalyst utilized is solely a ruthenium compound together with the quaternary base or salt. Likewise, when the catalyst system employed comprises, for example, only cobalt iodide and ruthenium dioxide no ethanol is formed. Furthermore, a high degree of conversion of methanol to the desired ethanol is achieved in this process. Also the stability of this catalyst system is such that it can be conveniently recovered from the reaction mixture and recycled to the process.

Generally, with regard to the metallic components of the catalyst system it will contain from about 20 to about 80 mole percent of the ruthenium compound with the balance being cobalt iodide based on the total number of moles of the ruthenium compound and the total number of moles of the cobalt compound in the system. Preferably, the catalyst system will contain about equimolar amounts of the ruthenium and cobalt compounds.

A wide variety of ruthenium compounds may be utilized in the catalyst system of this invention. For instance, the ruthenium may be added to the reaction mixture in an oxide form, as in the case of, for example, ruthenium(IV) oxide, hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, anhydrous ruthenium(III) chloride and ruthenium nitrate, or as the salt of a suitable organic carboxylic acid, for example, ruthenium(III) acetate, ruthenium(III) propionate, ruthenium butyrate, ruthenium(III) trifluoroacetate, ruthenium octanoate, ruthenium napththenate, ruthenium valerate and ruthenium(III) acetylacetonate. The ruthenium may also be added to the reaction zone as a carbonyl or hydrocarbonyl derivative. Here, suitable examples include triruthenium dodecacarbonyl, hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Cobalt-containing compounds useful in the ruthenium-cobalt bimetallic catalyst of this invention include cobalt(II) iodide, cobalt(II) bromide and cobalt(II) chloride. If desired, cobalt(II) iodide may be generated in situ by adding to the reactor cobalt and elemental iodine or cobalt and hydrogen iodide.

Quaternary phosphonium salts suitable for use in this process have the formula:

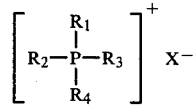

where $R_1$, $R_2$, $R_3$ and $R_4$ are organic radicals, particularly alkyl, aryl or alkaryl radicals bonded to the phosphorous atom, and X is an anionic species. The organic radicals useful in this instance include those alkyl radicals having 1 to 20 carbon atoms in a branched or linear alkyl chain; they include, for example, the methyl, ethyl, n-butyl, iso-butyl, octyl, 2-ethylhexyl and dodecyl radicals. Tetraoctylphosphonium bromide and tetrabutylphosphonium bromide are typical examples presently in commercial production. The corresponding quaternary phosphonium and ammonium acetates, hydroxides, nitrates, chromates, tetrafluoroborates and other halides, such as the corresponding chlorides, and iodides, are also satisfactory in this instance. Also useful are the corresponding quaternary ammonium bases and salts of the above series of compounds.

Equally useful are the phosphonium and ammonium salts containing phosphorus or nitrogen bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$-$C_{10}$ alkyl substituents, bonded to the phosphorus or nitrogen atom through the aryl function.

Illustrative examples of suitable quaternary phosphonium and ammonium bases and salts include tetrabutylphosphonium bromide, tetraoctylphosphonium bromide, heptyltriphenylphosphonium bromide, tetrabutylphosphonium iodide, tetrabutylphosphonium chloride, tetrabutylphosphonium nitrate, tetrabutylphosphonium hydroxide, tetrabutylphosphonium chromate, tetrabutylphosphonium tetrafluoroborate, tetrabutylphosphonium acetate, tetrabutylammonium bromide and tetramethylammonium hydroxide, pentahydrate and trimethyldodecylammonium bromide.

The preferred quaternary salts are generally the tetralkylphosphonium or alkyl-triaryl salts containing alkyl groups having 3-8 carbon atoms, such as butyl, hexyl and octyl and where the aryl group is phenyl. Tetrabutylphosphonium salts, such as tetrabutylphosphonium bromide, constitute a preferred group of tetraalkylphosphonium salts for the practice of this invention.

Preferred tetrabutylphosphonium salts or bases include the bromide, chloride, iodide, acetate, the chrome salts and hydroxide base. Preferred alkyl-triaryl phosphonium salts include, for example, heptyltriphenylphosphonium bromide, butyltriphenylphosphonium bromide, and methyltriphenylphosphonium bromide, as well as the corresponding chlorides.

Generally, in the catalyst system the molar ratio of the ruthenium compound to the quaternary phosphonium or ammonium base or sale will range from about 1:0.01 to about 1:100 or more and, preferably, will be from about 1:0.05 to about 1:20.

The quantity of ruthenium compound employed in the instant invention is not critical and may vary over a wide range. In general, the novel process is desirably conducted in the presence of a catalytically effective quantity of the active ruthenium species and of the cobalt iodide which gives the desired product in reasonable yield. The reaction proceeds when employing as little as about $1 \times 10^{-6}$ weight percent, and even lesser amounts, of ruthenium together with about $1 \times 10^{-6}$ weight percent or less of cobalt, basis the total weight of the reaction mixture. The upper concentration is dictated by a variety of factors including catalyst cost, partial pressures of carbon monoxide and hydrogen, operating temperature etc. A ruthenium concentration of from about $1 \times 10^{-5}$ to about 5 weight percent in conjunction with a cobalt concentration of from about $1 \times 10^{-5}$ to about 5 weight percent, based on the total weight of reaction mixture is generally desirable in the practice of this invention.

The temperature range which can usefully be employed in these syntheses is a variable dependent upon other experimental factors, including the pressure, and the concentration and choice of a particular species of ruthenium catalyst among other things. The range of operability is from about 150° to 350° C. when superatmospheric pressures of syngas are employed. A narrow range of 180°-250° C. represents the preferred temperature range.

Superatmospheric pressures of 500 psi or greater lead to substantial yields of ethanol by the process of this invention. A preferred operating range is from 2000 psi to 10,000 psi, although pressures above 10,000 psi also provide useful yields of ethanol.

The relative amounts of carbon monoxide and hydrogen which may be initially present in the syngas mixture can be varied widely. In general, the mole ratio of CO to $H_2$ is in the range from about 20:1 up to about 1:20, preferable from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Higher alcohols and carboxylic acid esters may also be formed while carrying out the process of this invention. Most often these derivatives are n-propanol, methyl formate, methyl acetate, ethyl acetate, ethyl ether, etc. The major by-products of the process of this invention such as the higher molecular weight alcohols and carboxylic acid esters, are, of course, also useful compounds and major articles of commerce. The higher alcohols, the carboxylic acid esters and ethers can easily be separated from one another by conventional means, e.g., fractional distillation in vacuo.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the ethanol product, and after recovery of the alcohol and other products, a fraction rich in ruthenium catalyst components may then be recycled to the reaction zone, if desired, and additional products generated.

The products have been identified in this work by one or more of the following analytical procedures, viz, gas-liquid phase chromatograph (GLC), infrared (IR), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psi).

The following examples illustrate the novel process of this invention.

EXAMPLE 1

A glass liner reactor was charged with 0.38 g (2.0 mmoles) of hydrated ruthenium oxide, 0.63 g (2.0 mmoles) of cobalt(II) iodide, 3.53 g (8 mmoles) of n-heptyltriphenylphosphonium bromide and 20 ml of methanol. The glass liner was placed in a stainless steel reactor, the reactor was purged of air and pressured to 1500 psi with a mixture of carbon monoxide and hydrogen (1:1 molar) and then heated to 200° C. while it was agitated by rocking. The pressure was brought up to 4000 psi and held at 200° C. for 18 hours. As the reaction proceeded the pressure dropped to 3220 psi.

The reaction was stopped after 18 hours and the reactor cooled to room temperature (final pressure—1790 psi). An off-gas sample was collected and excess gas was vented after which 24.1 g of a reddish-brown product was collected.

Analysis of the liquid product by GLC showed the following product yield composition:
- 64 mole % ethanol
- 5 mole % n-propanol
- 9 mole % methyl formate
- 8 mole % ethyl acetate
- 3 mole % ethyl ether The methanol conversion was calculated to be 59 mole.

A typical off-gas sample showed the presence of:
- 29.1% hydrogen
- 5.6% carbon monoxide
- 9.3% methane
- 49.3% carbon dioxide
- 0.7% ethanol

EXAMPLES 2 AND 3

Following the general procedure of Example 1 two additional catalyst systems were employed in preparing ethanol from methanol by the process of this invention. Details relating to the catalyst composition and other conditions are set out in Table 1 which follows.

The data in these examples indicate that a high degree of methanol conversion and a high degree of selectivity to ethanol in the liquid product was achieved.

TABLE I

HOMOLOGATION OF METHANOL

| Example | Catalyst Composition | MeOH Conversion (Mole %) | Selectivity (Mole %) | | | | | |
|---|---|---|---|---|---|---|---|---|
| | | | EtOH | n-PrOH | MeOOCH | MeOAc | EtOAc | Et$_2$O |
| 2[a] | RuO$_2$—n-C$_7$H$_{15}$Ph$_3$PBr—CoI$_2$ | 61 | 68 | 5 | 18 | 12 | 5 | 5 |
| 3[b] | RuO$_2$—n-Bu$_4$PBr—CoI$_2$ | 80 | 56 | 4 | 5 | 10 | 12 | 2 |

[a]Run Conditions: 0.38 g (2.0 mmoles) RuO$_2$; 3.53 g (8 mmoles) n-C$_7$H$_{15}$Ph$_3$PBr; 1.26 g (4.0 mmoles) CoI$_2$; MeOH 20 ml; time 18 hours; temp. 200° C., initial pressure 4000 psi; H$_2$/CO (1:1 molar).
[b]Run Conditions: 0.38 g (2.0 mmoles) RuO$_2$; 6.8 g (20 mmoles) n-Bu$_4$PBr; 1.26 g (4.0 mmoles) CoI$_2$; MeOH 20 ml; time 18 hours; temp. 200° C.; initial pressure 4000 psi; H$_2$/CO (1:1 molar).

EXAMPLE 4

In this comparative example the experimental procedure of Example 1 was followed. The reactor was charged with 0.38 g (2.0 mmole) of hydrated ruthenium(IV) dioxide, 3.53 g (8.0 mmoles) of n-heptyltriphenylphosphonium bromide and 20 ml of methanol. No cobalt(II) iodide was present in this run. After pressuring to 1500 psi with a mixture of carbon monoxide and hydrogen (1:1 molar), the reactor was heated to 200° C. while it was agitated by rocking. The pressure was then raised to 4000 psi with the same carbon monoxide-hydrogen mixture and maintained at 200° C. for 18 hours, as the reaction proceeded the pressure dropped to 3700 psi. The reactor was cooled rapidly and the residual pressure (2090 psi) was noted. Excess gas was removed by depressuring and a reddish-brown liquid product 21.7 g recovered from the glass reactor liner.

Analysis of the liquid product by GLC showed the following product yield composition:
- 30 mole % ethanol
- 2 mole % n-propanol
- 14 mole % methyl formate
- 7 mole % methyl acetate The methanol conversion was 26 mole percent.

The results of this experiment show the low yield of ethanol as well as the low conversion of methanol when cobalt(II) iodide is omitted from the catalyst system.

EXAMPLE 5

In this comparative example the experimental procedure of Example 1 was followed. The reactor was charged with 0.38 g (2.0 mmoles) of hydrated ruthenium dioxide, 0.25 g (1.0 mmole) of iodine and 15 ml of methanol. No quaternary phosphonium or ammonium base or salt and no cobalt(II) iodide was present in this run. Using a 1:1 (molar) mixture of carbon monoxide and hydrogen the reactor was pressured to 1000 psi and heated to a temperature of 200° C. while it was agitated by rocking. Next the reactor was pressured to 4000 psi using the same carbon monoxide-hydrogen mixture and held at 200° C. for 18 hours. At the end of the reaction period the pressure was 3525 psi.

The reactor was cooled to room temperature, an off-gas sample was taken and the excess gas released. The reddish-brown liquid product which was recovered (9.1 g) was analyzed by GLC, product composition was as follows:
- 75 mole % ethanol
- 2 mole % n-propanol
- 9 mole % methyl formate
- 2 mole % methyl acetate
- 1 mole % ethyl ether The methanol conversion was 26 mole percent.

The data in this experiment show the very low conversion of methanol achieved when no quaternary salt or cobalt(II) iodide is present in the catalyst system.

EXAMPLE 6

The experimental procedure of Example 1 was employed in this comparative example. The reactor was charged with 0.38 g (2.0 mmoles) of hydrated ruthenium dioxide, 3.53 g (8.0 mmoles) of n-heptyltriphenylphosphonium bromide, 0.25 g (1.0 mmole) of iodine and 15 ml of methanol. No cobalt(II) iodide was present in this example. The reactor was pressured to 1000 psi using a 1:1 molar mixture of carbon monoxide and hydrogen and heated to a temperature of 200° C. while it was agitated by rocking. Using the same carbon monoxide-hydrogen mixture the reactor was pressured to 4000 psi and maintained at 200° C. for 18 hours. At the end of the reaction period the pressure was 3720 psi.

The reactor was cooled to room temperature, an off-gas sample was taken and excess gas was vented. A reddish-brown liquid product (16.2 g) which was recovered was analyzed by GLC showed the following product composition:
- 52 mole % ethanol
- 7 mole % n-propanol
- 15 mole % methyl formate
- 7 mole % methyl acetate 1 mole % ethyl ether Methanol conversion was 19 mole percent. These results show that a very low degree of methanol conversion resulted when cobalt(II) iodide was not present in the reaction mixture.

What is claimed is:

1. A process for preparing ethanol which comprises contacting a mixture of carbon monoxide, hydrogen and methanol with a catalyst system comprising a ruthenium compound, a quaternary phosphonium or ammonium base or salt and a cobalt compound selected from the group consisting of cobalt(II) iodide, cobalt(II) bromide and cobalt(II) chloride at a pressure of 500 psi or greater and at a temperature of at least 150° C.

2. The process of claim 1 wherein the process is conducted at a pressure of about 2000 psi to about 10,000 psi.

3. The process of claim 1 wherein the process is conducted at a temperature of about 180°–250° C.

4. The process of claim 1 wherein the said ruthenium compound is selected from the group consisting of anhydrous ruthenium(IV) dioxide, ruthenium(IV) dioxide hydrate, ruthenium(VIII) tetraoxide, ruthenium(III) trichloride, ruthenium acetate, ruthenium propionate, ruthenium(III) acetylacetonate and triruthenium dodecocarbonyl.

5. The process of claim 1 where the said ruthenium compound is ruthenium(IV) dioxide hydrate.

6. The process of claim 1 wherein the said ruthenium compound is ruthenium(III) trichloride.

7. The process of claim 1 wherein the said quaternary is a tetraalkylphosphonium salt.

8. The process of claim 1 wherein the said quaternary is an alkyl-triarylphosphonium salt.

9. The process of claim 1 wherein the said quaternary is a tetrabutylphosphonium salt.

10. The process of claim 1 wherein the said quaternary is an alkyl-triphenylphosphonium salt.

11. The process of claim 1 wherein the said quaternary is selected from the group consisting of tetrabutylphosphonium chloride, tetrabutylphosphonium bromide, tetrabutylphosphonium iodide, tetrabutylphosphonium acetate, tetrabutylphosphonium chromate and tetrabutylphosphonium hydroxide.

12. The process of claim 1 wherein the said quaternary is tetrabutylphosphonium bromide.

13. The process of claim 1 wherein the said quaternary is selected from the group consisting of heptyltriphenylphosphonium bromide, heptyltriphenylphosphonium chloride, and methyltriphenylphosphonium bromide.

14. The process of claim 1 wherein the said quaternary is heptyltriphenylphosphonium bromide.

15. The process of claim 1 wherein the said ruthenium compound is hydrated ruthenium(IV) dioxide and the said quaternary is tetrabutylphosphonium bromide.

16. The process of claim 1 wherein the said ruthenium compound is hydrated ruthenium(IV) dioxide and the said quaternary is heptyltriphenylphosphonium bromide.

17. The process of claim 1 wherein the said quaternary is a quaternary phosphonium base.

18. The process of claim 17 wherein the said quaternary is tetrabutylphosphonium hydroxide.

19. The process of claim 1 wherein the said ruthenium compound is ruthenium oxide and the said quaternary is a quaternary phosphonium base.

20. The process of claim 1 wherein the said quaternary is a quaternary ammonium base.

21. The process of claim 20 wherein the said quaternary is tetramethylammonium hydroxide.

22. The process of claim 1 wherein the said ruthenium compound is ruthenium oxide and the said quaternary is a quaternary ammonium base.

* * * * *